United States Patent [19]

Atala

[11] Patent Number: 5,571,119
[45] Date of Patent: Nov. 5, 1996

[54] RETRACTABLE SUTURE NEEDLE WITH SELF-CONTAINED DRIVER

[75] Inventor: Anthony Atala, Weston, Mass.

[73] Assignee: Children's Medical Center Corporation, Boston, Mass.

[21] Appl. No.: 437,963

[22] Filed: May 10, 1995

Related U.S. Application Data

[63] Continuation of Ser. No. 142,218, Oct. 25, 1993, abandoned.

[51] Int. Cl.$^6$ .................................................. A61B 17/04
[52] U.S. Cl. ........................... 606/146; 606/144; 606/145
[58] Field of Search ............................ 606/139, 145–147

[56] References Cited

U.S. PATENT DOCUMENTS

| | | | |
|---|---|---|---|
| 1,822,330 | 9/1931 | Ainslie | 606/145 |
| 2,008,251 | 7/1935 | Hillebrand | 606/146 |
| 2,336,689 | 12/1943 | Karle | 606/146 |
| 2,414,746 | 1/1947 | Karle | 606/146 |
| 2,457,379 | 12/1948 | Kallenbach | 606/146 |
| 3,638,654 | 2/1972 | Akuba | 128/340 |
| 4,221,212 | 9/1980 | Miller . | |
| 4,373,530 | 2/1983 | Kilejian | 128/334 |
| 4,440,171 | 4/1984 | Nomoto et al. | 606/145 |
| 4,527,564 | 7/1985 | Eguchi et al. | 606/145 |
| 5,222,977 | 6/1993 | Esser | 606/144 |
| 5,224,948 | 6/1993 | Abe et al. . | |

FOREIGN PATENT DOCUMENTS

| | | |
|---|---|---|
| 0315371A3 | 10/1988 | European Pat. Off. . |
| 0567130A1 | 4/1993 | European Pat. Off. . |

OTHER PUBLICATIONS

"Marlow Introduces the Clarke Needle Forcep: A Suture Grasper And A Needle Driver In A Single Instrument," Marlow Surgical Technologies, Inc. (1993), Advertisement.

*Primary Examiner*—Gary Jackson
*Attorney, Agent, or Firm*—Thomas J. Engellenner; Lahive & Cockfield

[57] ABSTRACT

Methods and apparatus for suturing in physically confined and visually restricted areas are disclosed. Suturing instruments are described that serve to deliver suture material through biological tissue by extending and retracting the distal portion of the instrument through the tissue. Suture needles are described that include structure for piercing through biological tissue to a position on the opposite side of the anastomotic site structure for delivering suture material through the tissue. In this way, a stitch is formed as the suture needle retracts. In one embodiment, the suture needle includes a notch located on the needle surface which can receive a loop of suture material. Upon passing the suture needle through the tissue, the suture material can be seated within the notch so that the suture material is drawn through the tissue as the needle is retracted. The needle can include a coupling mechanism that mounts the needle for pivoting action in response to a linear actuating motion of a rod. The suture needle can further have an interior passage extending from the end of the needle to the means for receiving suture. The interior passage can be the dimensioned for receiving suture and an optional guide wire, where the guide wire guides the suture through the passage and into the means for receiving suture.

24 Claims, 7 Drawing Sheets

RETRACTABLE SUTURE NEEDLE WITH SELF-CONTAINED DRIVER

BACKGROUND OF THE INVENTION

This application is a continuation of application Ser. No. 08/142,218, filed on Oct. 25, 1993 now abandoned.

The present invention relates generally to the field of surgical devices and more specifically to surgical devices and methods for endoscopic surgical suturing.

Many surgical procedures, including endoscopy and catheter-based procedures, require the surgeon to work through narrow channels. These narrow channels severely restrict the surgeon's ability to maneuver at the surgical site. As a result, surgery using these techniques is more burdensome and time consuming than conventional surgery. For surgeons operating under these restricted conditions, a particularly demanding procedure is suturing. Ordinarily, suturing is a simple and reliable method for joining tissue. However, endoscopic suturing is complicated because the surgeon lacks mobility to maneuver the needle through the tissue at the anastomotic site. Although techniques have been developed as alternatives to suturing, none have proven to provide the simplicity and the safety of the conventional suturing procedure.

The conventional suture needle is a curved needle with a point at one end and with a length of suture connected at the other end. During the conventional suturing procedure, the surgeon grips the needle and the suture with a scissor-like instrument called a needleholder. Using the needleholder, the surgeon manipulates the needle through the tissue and pulls the needle and the suture completely through the tissue to form a stitch. Each time the needle and suture pass through the tissue a stitch is formed. After the appropriate number of stitches are made, the surgeon ties a knot in the suture and cuts off the excess length with a pair of surgical scissors.

The suturing technique described above works well during conventional "open" surgical procedures. In these "open" procedures, the surgeon uses a scalpel or a similar instrument to make an incision in the patient. This incision enables the surgeon to access the anastomotic site. To allow the surgeon to perform the suturing procedure, the incision must be made large enough to obtain adequate exposure, and must be large enough to provide sufficient maneuvering room to permit suturing. Therefore, this incision is often quite large and inflicts substantial tissue damage on the patient. The incision therefore, compounds the patient's injury and substantially increases the recovery time from a surgical procedure.

To avoid the large incision of the "open" surgical procedure, surgeons have developed endoscopic surgical techniques. For example, laparoscopic surgery, a particular endoscopic technique, allows the surgeon to enter the patient's abdominal cavity through one or more minor incisions in the patient's abdominal tissue wall. Each incision is approximately a centimeter in length. Typically, the abdominal wall is penetrated with a surgical trocar, which allows for the placement of a laparoscopic tubular port through the small incision and into the abdomen. The operation is then performed through these laparoscopic ports. The small size of each of these incisions reduces the trauma of surgery and substantially reduces the patient's recovery time.

The conventional laparoscopic suturing procedure is an adaptation of the "open" suturing procedure described above. A video endoscope is placed through a laparoscopic port within the abdomen to display the abdominal interior. Through one of the laparoscopic ports, the curved suture needle is positioned within the patient's abdominal cavity close to the surgical site. The surgeon uses special endoscopic instruments to grip the needle and the suture. In one example, an endoscopic needleholder and an endoscopic blunt grasper are extended into the abdomen. While viewing the anastomotic site on a video display, the surgeon manipulates the needleholder and the grasper, to grip the suture needle and to pass the needle completely through the tissue segments, thus forming a stitch.

This adaptation of the "open" suturing procedure has proved less than satisfactory, for several reasons. Firstly, endoscopic instruments are much longer than conventional suturing instruments. This added length exaggerates certain hand movements of the surgeon. For example, a small twist of the surgeon's hands moves the distal tip of the instrument in a large arc. The surgeon must constantly compensate for this effect by restricting his or her hand motions to a fraction of what he or she normally would use. Secondly, the surgeon is confined by the narrow ports through which he or she operates. These ports, typically 10 to 11 mm wide, are particularly restrictive of the surgeon's lateral movement. Thus, the endoscopic surgeon must further compensate for his or her restricted lateral mobility, by limiting his or her lateral movements during the procedure. These restrictions make endoscopic suturing a more burdensome and difficult technique than conventional "open" surgery suturing.

The endoscopic surgeon's vision is also restricted. The video endoscope placed within the patient only provides a two dimensional view of the surgical area. Therefore, the surgeon lacks depth perception and must use trial and error to establish the exact position of the objects displayed on the video monitor. This becomes particularly burdensome when the surgeon is switching between instruments. Endoscopic suturing is especially grueling because the surgeon must release and relocate the suture needle each time he or she passes the needle through the tissue. Once the needle is relocated, the surgeon must reposition the needle correctly within the needleholder to begin forming the next stitch. All these manipulations must be performed with a very restricted view of the anastomotic site and without any perception of depth.

To aid the endoscopic surgeon, alternative devices have been developed to join tissue. One common alternative device is the endoscopic stapler. Typically, these staplers have a pistol grip connected to a slender extension arm that has a stapler mechanism connected at the distal end. The stapler mechanism is operated by a trigger located on the pistol grip. Each time the surgeon squeezes the trigger, the stapler mechanism pinches together a surgical staple and the tissue between the pinchers is joined. The endoscopic stapler allows the surgeon to join tissue without using the suturing technique. However, the staple technique differs from the suture technique in important ways. The stapler does not form a continuous seam along the joined tissue, instead it joins the tissue at the discrete points where the staples attach. Furthermore, the staples left within the patient are typically less biodegradable than the suture thread which remains after the suture operation. In addition, staples cannot be used with certain types of tissue, such as blood vessels, and numerous types of surgical procedures.

It is, therefore, an object of the present invention to provide a method and means for suturing tissue that is adapted for use with physically confined and visually restricted surgical procedures.

It is a further object of the present invention to provide an apparatus and method for suturing that reduces the amount of lateral motion necessary to form a stitch.

It is still a further object of the present invention to provide a method and means for forming stitches in tissue without passing a needle completely through the tissue to be joined.

It is another object of the invention to provide method and means for forming stitches in tissue that avoids releasing the suture needle and relocating the suture needle each time a stitch is formed.

SUMMARY OF THE INVENTION

Methods and apparatus for suturing in physically confined and visually restricted areas are disclosed. Suturing instruments are described that serve to deliver suture material through biological tissue by extending and retracting the distal portion of the instrument through the tissue. Suture needles are described that include structure for piercing through biological tissue to a position on the opposite side of the anastomotic site structure for delivering suture material through the tissue. In this way, a stitch is formed as the suture needle retracts. In one embodiment, the suture needle includes a notch located on the needle surface which can receive a loop of suture material. Upon passing the suture needle through the tissue, the suture material can be seated within the notch so that the suture material is drawn through the tissue as the needle is retracted.

One advantage of the notched suture needle is that it does not require the surgeon to pass the needle completely through the tissue to form a stitch. This reduces the motion necessary to perform the suturing procedure. Furthermore, it reduces the number of times the operating surgeon must release, locate and grip the needle.

In another aspect of the invention the suture needle has a notch with a latch that extends over the notch to prevent the notch from catching on or tearing tissue during the suturing operation. An advantage of the latch is that it prevents tearing when the needle is passed through delicate membranes, such as blood vessels, and further works to prevent the suture from slipping out of the notch.

Endoscopic suture instruments are disclosed that are constructed for insertion into an endoscopic port or into an anatomical channel, and to position close to an anastomotic site the distal portion of the instrument. The distal portion of the instrument includes structure that forms a stitch by extending into and retracting from, biological tissue.

The terms "endoscope" and "endoscopic" are used herein to broadly encompass instruments such as laparoscopes, cytoscopes, colonoscopes, sigmoidoscopes, arthroscopes, esophagoscopes, bronchoscopes, gastroscopes, thoracoscopes, peritoneoscopes, culdoscopes, catheters, and the like, which are designed to penetrate a body structure, cavity or lumen and to permit a clinician to view the internal body structure and to effect a surgical procedure or other therapeutic action.

In one embodiment of the invention, the notched suture needle is connected to a needle driver that has an extension arm with a pivoting linkage assembly. This assembly pivots the needle when a rod, connected to the assembly, is pushed forward (or pulled backward). In this aspect, the invention reduces the lateral motion necessary, to drive the needle into the tissue. An advantage of this linkage assembly is that the suture needle is responsive to a linear driving movement, thereby providing a linearly-actuated suturing apparatus and method facile enough to permit use through laparoscopic ports. In a further embodiment, the needle driver can include a pistol grip and a rotating cuff; whereby the cuff allows the extension arm to be rotated to select a particular angular orientation for the suture needle.

In another embodiment of the invention, the needle driver has a socket adapted for receiving a disposable notched suture needle.

In yet another embodiment of the invention, the needle is disposable and has a socket mounted at one end for detachably mounting to a needle driver.

In a further embodiment of the invention, a suture needle can have an interior passage and an opening near the pointed end. In such embodiments, the interior passage is large enough so that a strand of suture, alone or with an optional guide wire, can lit within the passage. The suture material can be fed to the site manually. Alternatively, the guide wire and suture can be coupled, typically by friction, and the suture can be guided through the passage and out of the opening, by moving the guide wire through the passage.

Moreover, the suture needle with the interior passage can be coupled to an extension arm with an interior passage, to form an assembly that can be used to deliver suture through the arm, into the needle passage, and out the needle opening. This embodiment can include an optional guide mechanism that extends through both interior passages and that can be used to guide a strand of suture through the arm and the needle and out the needle opening. The apparatus can further incorporate a linkage assembly that pivots the needle when an actuator, such as a plunger or a pistol grip, is driven to operate the linkage assembly.

DETAILED DESCRIPTION OF THE INVENTION

The present invention provides apparatus and methods for suturing tissue using a retractable suture needle. The invention is based, in part, on the principle that only the forward (or distal) portion of a needle must be passed through tissue in order to form a stitch. In one aspect, the distal end of a needle with a notched surface can pass through tissue, and can securely grip a loop of suture. The suture will be pulled through the tissue when the needle is retracted. By anchoring the suture on either side of the tissue, typically done by securing a ball of biocompatible material to the suture ends, a stitch is formed in the tissue.

Figure 1:
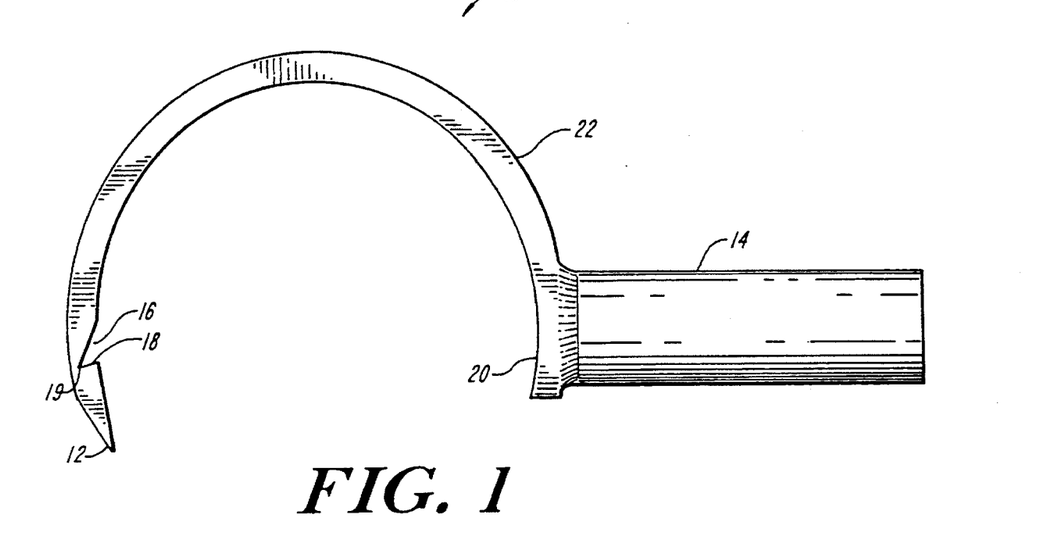
FIG. 1 illustrates a suture needle constructed according to the present invention.

FIG. 1 illustrates one embodiment of a suture needle 10 constructed according to the present invention. The needle has a pointed end 12, a coupling arm 14 and a notch 16 located between the pointed end 12 and the coupling arm 14. In the depicted embodiment, the notch 16 is positioned on the interior curved surface 20 of the needle 10 and the coupling arm 14 has a cylindrical shape suitable for mounting into a tubular sleeve. In the illustrated embodiment the notch 16 is located proximate to the distal end of needle 10. By positioning the notch 16 proximate to the distal end only the forward portion of needle 10 must pass through tissue in order for the notch 16 to receive a loop of suture. In use, suture is delivered through the tissue of the anastomotic site by a reciprocating motion of the needle 10.

The needle 10, depicted in FIG. 1 has an acicular and/or arcuate shape and is approximately 3 millimeters from point 12 to notch 16. As dimensioned the depicted needle 10 fits within an endoscopic port. It should be clear that the device can be constructed and practiced with other shapes and dimensions. In an alternative embodiment, the needle 10 has a flat, blade-like shape with the interior and exterior surfaces sharpened into cutting edges. The notch 16 can be located along either the interior or exterior cutting edge. In a further alternative embodiment, the needle 10 is dimensioned large enough to be gripped and manipulated by conventional surgical needleholders, for use in "open" surgical procedures. Further embodiments that do not depart from the essence of the present invention will be apparent to those skilled in the art of surgical device design and surgical procedures.

The notch 16 of the illustrated embodiment is dimensioned to receive a loop of suture and is shaped to keep the suture loop seated within the notch 16 as the needle is retracted through the tissue. Particularly, the depicted notch 16 has an angled backwall 18 that directs the suture into the vertex 19 of the notch 16, as the needle 10 pulls the suture through the tissue. In alternative embodiments of the invention, the notch 16 can have a lip extending partially over the notch, to prevent the suture from slipping off the needle. Further, the notch 16 can be constructed so that the vertex 19 is pointed away from the distal end 12. This construction facilitates passing suture through the tissue as the needle passes into the tissue. In the preferred embodiment, a single notch 16 is located proximate to the distal end of needle 10, and on the interior curved surface 20. As illustrated in FIG. 1, the interior curved surface is smooth and regular except for the notch 16. Furthermore, the exterior curved surface 22 is also regular and smooth to prevent tearing as the needle 10 passes through the tissue.

Figure 2:
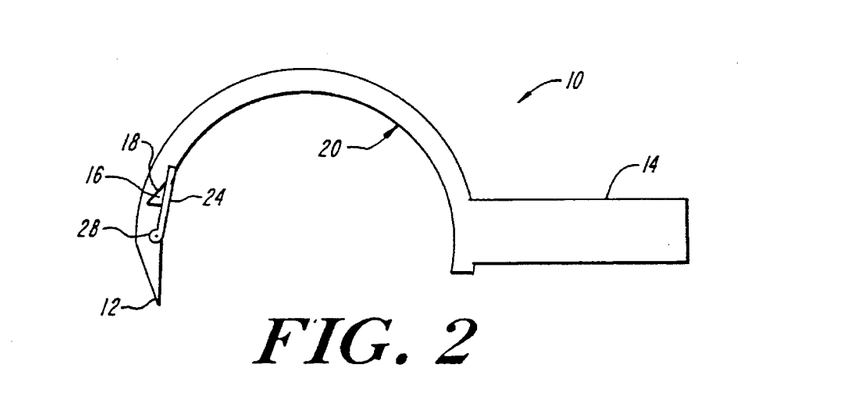
FIG. 2 is a cross-sectional illustration of a suture needle constructed according to the present invention with a latch in a closed portion.
Figure 3:
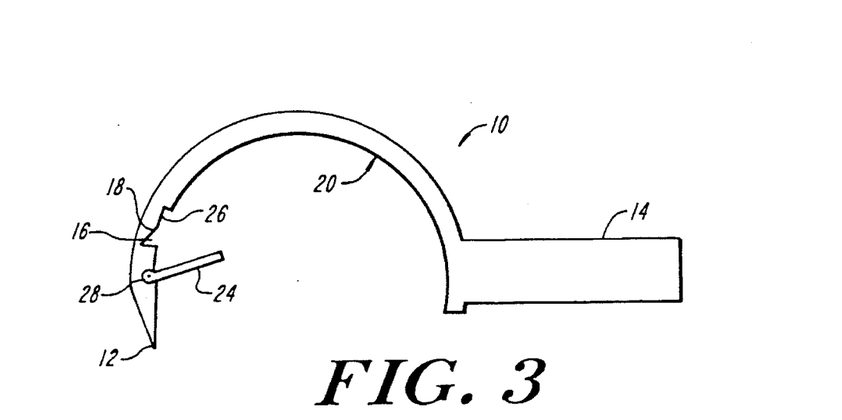
FIG. 3 is a further illustration of the suture needle of FIG. 2 showing the latch in an open position.

FIGS. 2 and 3 illustrate an alternative embodiment of the present invention that has a latch 24 that extends over the notch 16. In the embodiment shown, the latch 24 is biased closed to prevent the tearing of tissue as the needle is passed through and retracted from the tissue. As illustrated by FIG. 3, the latch 24 is moveable from the preferentially closed position to an open position for receiving a loop of suture. The spring hinge 28, is biased closed, and can be moved to an open position to expose the notch 16. In one example, the distal portion of the latch 24 can extend over an optional recess 26 so that a loop of suture thread can be fitted under the distal portion of the latch 24. By pulling back on the distal portion of the latch 24, the latch can be opened and the notch 16 exposed for receiving the suture. The optional recess 26, located on the interior curved surface, also can receive the unconnected end of the latch 24, in order to prevent latch 24 from opening or catching on tissue, when the needle is retracted through the tissue.

In the depicted embodiment, the latch 24 connects at hinge 28 between the notch 16 and the distal end 12. It is with the contemplation of the present invention, that the latch 24 be connected to the needle 10 between the notch 16 and the coupling arm 14. Furthermore, it should be apparent to those skilled in the art of surgical device design and surgical procedures, that other latch mechanisms are practicable with the present invention including, sliding latches, laterally swinging latches and preferentially open latches.

In a further aspect of the present invention, a notched suture needle is connected to the forward portion of an extension arm for use in endoscopic suturing.

Figure 4:
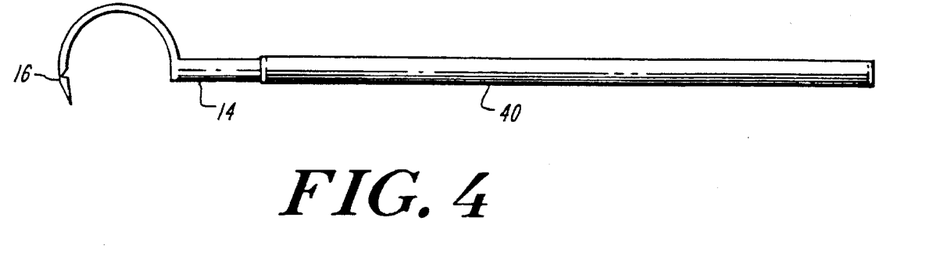
FIG. 4 illustrates a suture needle constructed according to the present invention and connected to an extension arm.

FIG. 4 illustrates an endoscopic instrument 39 for remote application of sutures according to the invention that includes the needle 10 and the extension arm 40. As depicted in FIG. 4, the coupling arm 14 of the needle 10 connects to the extension arm 40. In the preferred embodiment, the needle 10 is disposable and includes on the coupling arm 14, a coupling mechanism for temporarily mounting to the extension arm 40. Typically, the coupling arm 14 has an exterior thread for screwing into a threaded receptacle on the forward portion of the extension arm 40. However, other coupling mechanisms, are practicable with the invention, including forming the coupling arm 14 as a female receptacle that can receive and engage the distal portion of the arm 40. Furthermore, the coupling mechanism that joins the disposable needle with the extension arm 40 can be integrated into the distal portion of arm 40. For example, the coupling arm 14 can fit within a socket on the distal end of arm 40 or vice-versa The socket can include a set screw for locking the needle 10 into position within the socket. Other embodiments for joining the needle 10 to the arm 40 that do not depart from the essence of the present invention should be apparent to those skilled in the art of surgical devices and procedures.

The extension arm 40 is narrow and thin and adapted for fitting within a laparoscopic port. By manipulating the extension arm 40 through the laparoscopic port, the surgeon is able to perform the suturing procedure by passing the distal portion of the needle 10 through the tissue and seating a loop of suture within the notch 16 and retracting the needle 10 through the tissue.

Figures 5A, 5B:
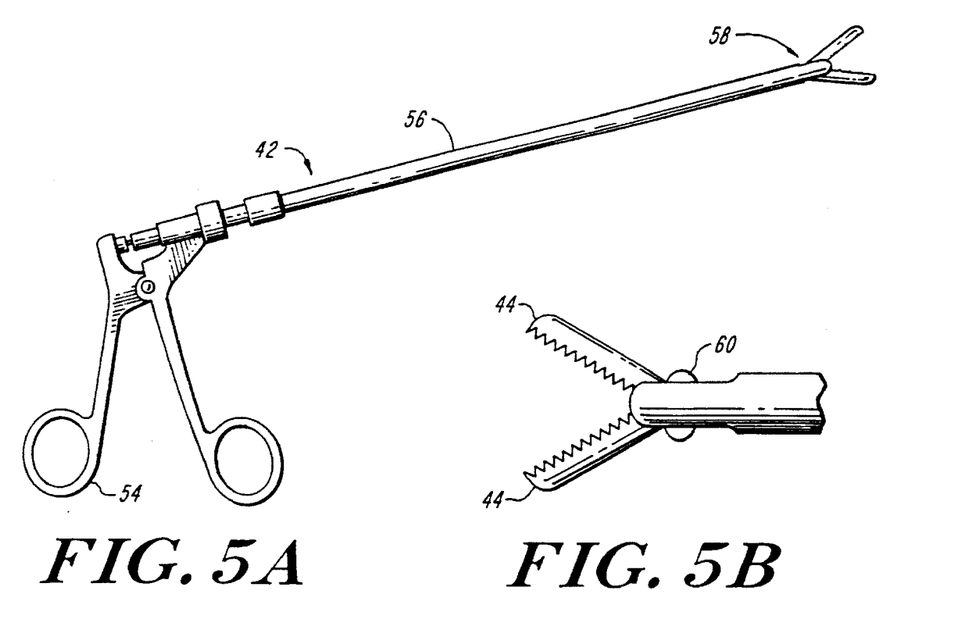
FIG. 5A illustrates a suture grip constructed according to the present invention.
FIG. 5B illustrates in more detail the forward portion of the suture grip.
Figure 5C:
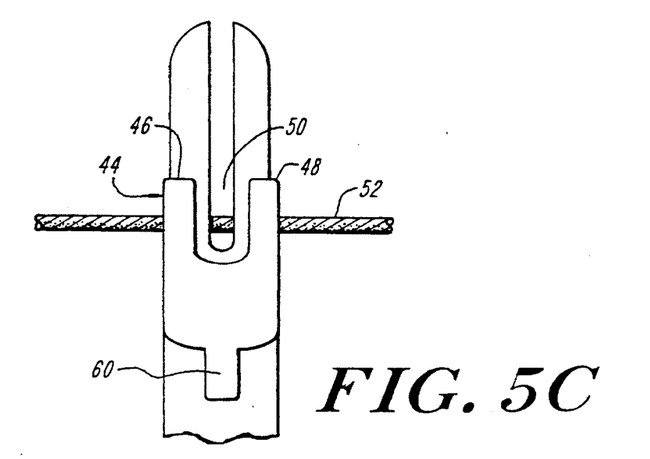
FIG. 5C is an overhead perspective of the forward portion of the suture grip.

FIGS. 5A, 5B and 5C illustrate from different perspectives a suture grip 42 for seating suture within the notch 16 of the needle 10. With reference to FIG. 5A, a side perspective of the grip 42 is shown depicting the scissor handle 54 connected at the rearward portion of the shall 56. The forward portion of the shaft 56 connects to the clamp 58, that has the hinge 60 and the U-shaped head 44. The scissor handle 54 operates the clamp 58 when the handle 54 is moved between an open and a closed position. The shaft 56 extends from the handle 54 and is dimensioned for slidably fitting within a laparoscopic port. At the distal end of the shaft 56 is the operable clamp 58 that moves between the clamped and the unclamped position.

FIG. 5B illustrates in greater detail a side perspective of the clamp 58. As illustrated, the clamp 58, has two identical and opposing forward head portions 44, that both connect to the hinge 60. The hinge 60, operated by the scissors grip 54, moves the two heads 44 between a clamped and an unclamped condition. In the illustrated embodiment, the heads 44 have serrated edges.

FIG. 5C illustrates from an overhead perspective, the clamp 58. Each head 44 is U-shaped and has two forward extending arms 46 and 48. An interior slot 50 extends approximately half-way through the head 44 between the arms 46 and 48. The rearward portion of the U-shaped head 44 connects to the hinge 60. In the FIG. 5C, the suture material 52 is gripped by the arms 46 and 48, and extends across the interior slot 50. The slot 50 can be dimensioned to slide over the needle 10, so that the needle 10 fits between the arms 46 and 48, and between the suture 52 and the U-shaped head 44.

With reference to FIGS. 4 and 5A–5C, an endoscopic suturing procedure according to the invention can be explained. In operation, the surgeon extends an endoscope into the patient through an endoscopic port. When the anastomotic site is displayed on video the surgeon extends the instrument 39 into a second laparoscpoic port and the suture grip 42 into a third laparoscopic port. The surgeon views the video display of the surgical site, while manipulating the forward portion of arm 40. Arm 40 is manipulated until the needle 39 penetrates through the tissue. When the notch 16 extends through the tissue, the surgeon slides the head 44 of gripping suture 52, over the distal portion of needle 10 and seats the suture 52 into the notch 16. The surgeon retracts the needle 10 through the tissue, and the suture is pulled through the tissue segments. Typically, the surgeon withdraws the suture grip 42 from the laparoscopic port, and extends an endoscopic clamp down the port and into the abdomen. The clamp is used to attach a ball of biocompatible material to one side of the suture, to prevent the suture from being pulled out of the tissue. Typically, the surgeon continues the suture procedure by placing the suture grip 42 back into the abdomen, gripping the suture and passing the forward portion of the needle 10 through the opposite side of the tissue. The surgeon seats suture into the notch 16, and retracts needle 10 back through the tissue. The surgeon continues this process until the appropriate number of stitches in entered. The final stitch is clamped with an anchor ball as previously described.

It should be apparent to those skilled in the art of surgical procedure, that other techniques for suturing tissue are practicable with the present invention, including using conventional suture grips to form a loop of suture for fitting into notch 16. This and other variations are within the scope of the present invention.

Figure 6A:
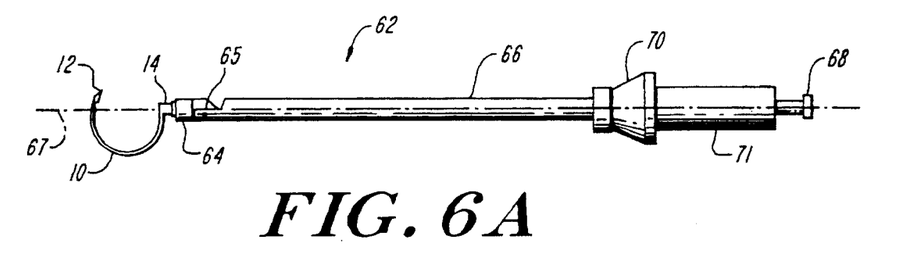
FIG. 6A illustrates a suture needle constructed according to the present invention and connected to a needle driver constructed according to the present invention with a pivoting linkage assembly.
Figure 6B:
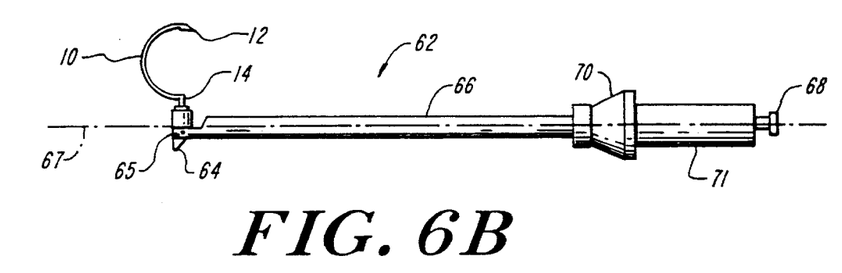
FIG. 6B illustrates the apparatus of FIG. 6A in pivoted position.

FIGS. 6A and 6B illustrate a needle 10 connected to an endoscopic needle driver 62 constructed according to the present invention. The driver 62 includes a pivoting linkage assembly 64, an extension arm 66, a connecting rod 68 and a handle 71. The longitudinal axis 67 extends through the driver 62, and the needle 10 can pivot about the pivot 65 relative to the axis 67. The needle 10 connects to the linkage assembly 64 of the needle driver 62. The linkage assembly 64 connects to the distal end of the extension arm 66 which is adapted for fitting within a laparoscopic port. Within the arm 66, the linkage assembly 64 connects between the needle coupling arm 14 and the connecting rod 68 which extends rearward from the linkage assembly 64 and projects outward from the handle 71. The linkage assembly 64 is a pivoting, mechanical assembly for converting the linear motion of the connecting rod 68 into a pivoting motion. For example, the proximal end of needle 10 can have a cam-shaped or sloping edge which, when engaged by a spherical or a similarily-shaped distal end of connecting rod 68, will have caused the needle 10 to rotate about the pivot 65. The needle driver also can include an optional rotating cuff 70, connected between the arm 66 and the handle 71. In use, the surgeon extends the driver 62 into a laparoscopic port to deliver the needle 10 to the anastomotic site. The optional cuff 70 allows the surgeon to adjust the angular orientation of the needle 10.

Figure 6C:
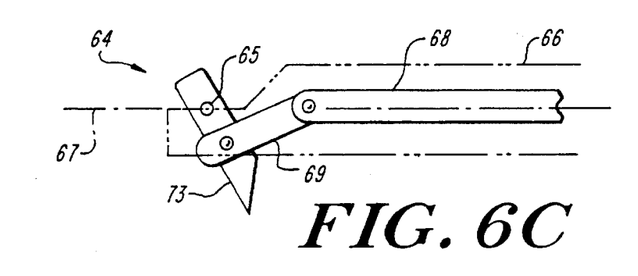
FIG. 6C illustrates in more detail the linkage assembly.

FIG. 6C illustrates in more detail one embodiment of a linkage assembly 64. As illustrated, the assembly 64 has a connecting link 69 that connects between the connecting rod 68 and a pivoting arm 73. As can be seen from the depicted embodiment, the pivoting arm 73 rotates about the pivot 65 when the connecting rod 68 moves forward in the arm 66. In one embodiment, the pivoting arm 73 can have a collet connected at its distal end for receiving and engaging the coupling arm 14 of the needle 10.

The action of the linkage assembly 64 is illustrated with reference to FIGS. 6A and 6B. As depicted, the assembly 64 is operated by pushing connecting rod 68 forward. The linear motion of the connecting rod 68 pivots the suture needle 10 about the pivot point 65 and relative to the longitudinal axis 67. In the preferred embodiment, the linkage assembly 64 is a spring operated pivot mechanism, that pivots the needle 10 when the connecting rod 68 is driven forward and that automatically returns the needle 10 to its original orientation when the rod 68 is released. As the needle 10 is driven forward, the point 12 penetrates the tissue to be joined, until the forward portion of the needle 10 extends through the tissue. As connecting rod 68 is released, the driver 62 retracts the forward portion of needle 10 through the tissue.

Figure 7:
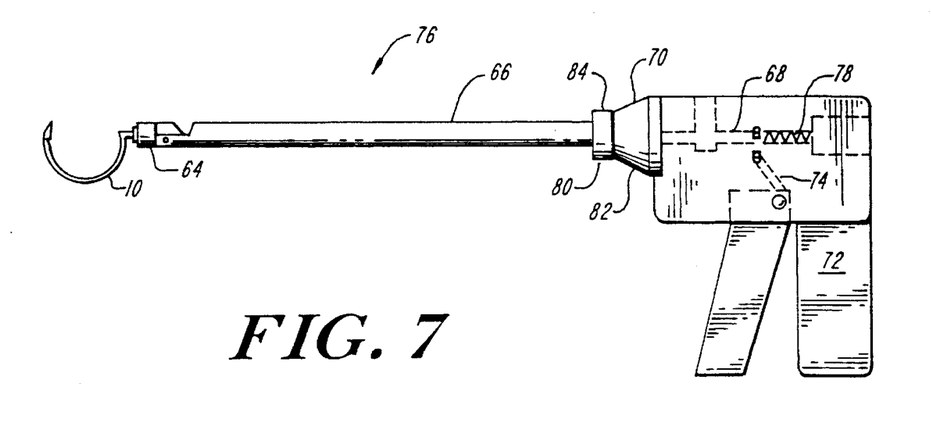
FIG. 7 illustrates a further alternative embodiment of the present invention having a pistol grip connected to the needle driver.

FIG. 7 illustrates a further needle driver 76 constructed according to the present invention. As depicted, a pistol grip 72 connects to the rearward portion of the rotating cuff 70. The grip 72 has a mechanical lever arm 74 for driving the connecting rod 68 forward to operate the linkage assembly 64.

As further illustrated, the mechanical lever arm 74 attaches to the connecting rod 68 in the pistol grip 72. The connecting rod 68 connects to the linkage assembly 64 at the forward portion of the needle driver 76. The extension arm 66 connects between the linkage assembly 64 and the rotating cuff 70. With reference to FIG. 7, it can be seen that the pistol grip 72 will operate the linkage assembly 64 when the pistol grip 72 is moved from a open position to a closed position. When grip 72 is moved to the closed position, the linkage arm 74 drives the connecting rod 68 forward and operates the linkage assembly 64 to pivot the needle 10.

When grip 72 is released, the spring 78 retracts the connecting rod 68 and the linkage assembly 64 pivots the needle 10 back to the initial position.

With further reference to FIG. 7, the rotating cuff 70 is described. The rotating cuff 70 can have a forward portion 80 and a rearward portion 82. The forward portion 80 connects to the extension arm 66 and the rearward portion 82 connects to the grip 72. The rearward portion 82 can fit within the forward portion 80 and slide into an annular mount 84. The forward portion 80 can be free to rotate about the inner rearward portion 82. In use, the rotating cuff 70 allows for the selection of a particular angular orientation for the needle 10. Specifically, the surgeon grips the forward portion 80 that connects to the extension arm 66, and rotates the portion 80, and arm 66, until the needle 10 has the selected orientation. The rotating cuff 70 can include an optional ratchet assembly for selecting discrete angular orientations.

With reference to FIGS. 6 and 7, it can be seen that the needle driver can be fabricated from hygenic materials that can be sterilized after use, according to methods known in the art. In this way the needle drivers can be used in multiple procedures. Furthermore, the needle 10 can be a disposable needle that can temporarily couple to the driver and used can be used for single procedure.

Figure 8:
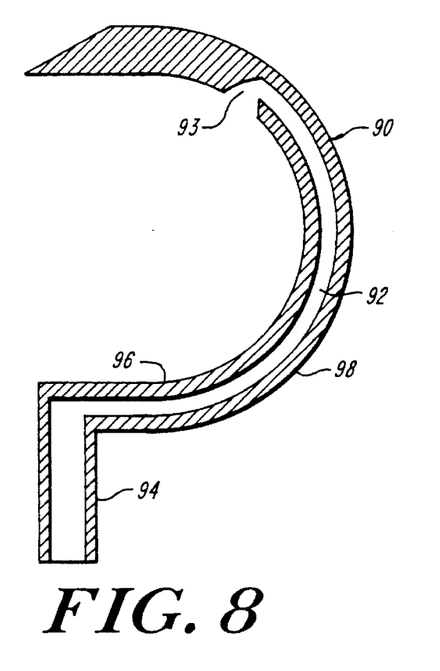
FIG. 8 illustrates a suture needle having an interior passage.

FIG. 8 illustrates a further embodiment of the present invention. FIG. 8 depicts a curved suture needle 90 having a hollow interior passage 92 extending between the coupling arm 94 and the port 93. The needle 90 can be constructed as a disposable needle that can have a coupling arm 94 constructed to mount temporarily to an extension arm, as described above. As illustrated by FIG. 8, the coupling arm 94 is hollow. The coupling arm 94, the interior chamber 92 and the notch 16 form an interior passage within the curved suture needle 90. The port 93 forms an opening in passage 92 through which suture material can be extended. In the illustrated embodiment, the port 93 is located at the distal portion of needle 90 and on the interior curved surface 96. It is within the contemplation of the present invention that the port 93 be located at different points along the interior curve surface 96 and the exterior curve surface 98.

The passage 92 can be dimensioned to accommodate a strand of suture. The suture can be inserted into the passage 92 through an opening in the coupling arm 94. The suture can be slid through the passage 92 and out the notch 93. It should be apparent to those skilled in the art of surgical device design, that the passage 92 can be dimensioned to accommodate any of the variety of suture materials available. This includes both thin thread-like suture materials, and thicker wire-like suture materials, or any of the other materials commonly used.

Figure 9:
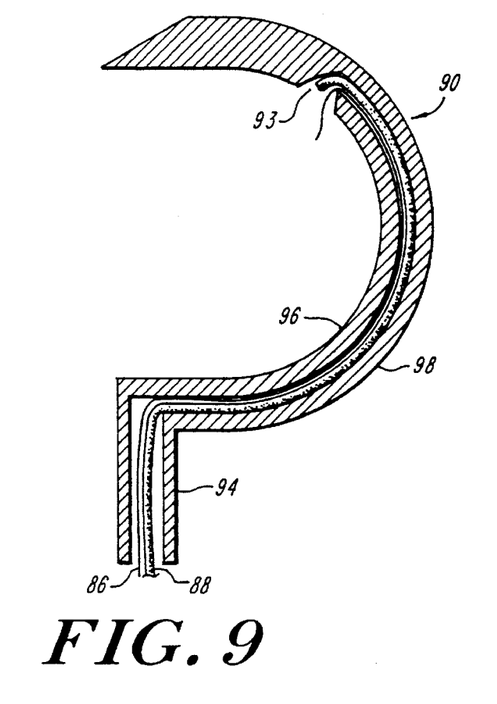
FIG. 9 illustrates a suture needle with an interior passage containing an optional guide wire and suture.

FIG. 9 illustrates the needle 90 fitted with suture 86 and the optional guide wire 88. As illustrated, the suture 86 and the guide wire 88 can be slid into the hollow passage 92 through the hollow coupling arm 94. The suture is in contact with the guide wire 88, and fitted within the chamber 92 so that the optional wire 88 and the suture 86 are slidable within the passage 92. In operation, the surgeon fits the suture 86 and the optional wire 88 into the passage 92. The needle 90 is passed through the tissue so that the port 93 penetrates through the tissue. The surgeon pushes the guide wire 88 into the needle 90 until the suture 86 extends from the port 93. The surgeon forms a stitch by gripping the suture 86 and retracting the needle 90 from the tissue.

Figure 10A:
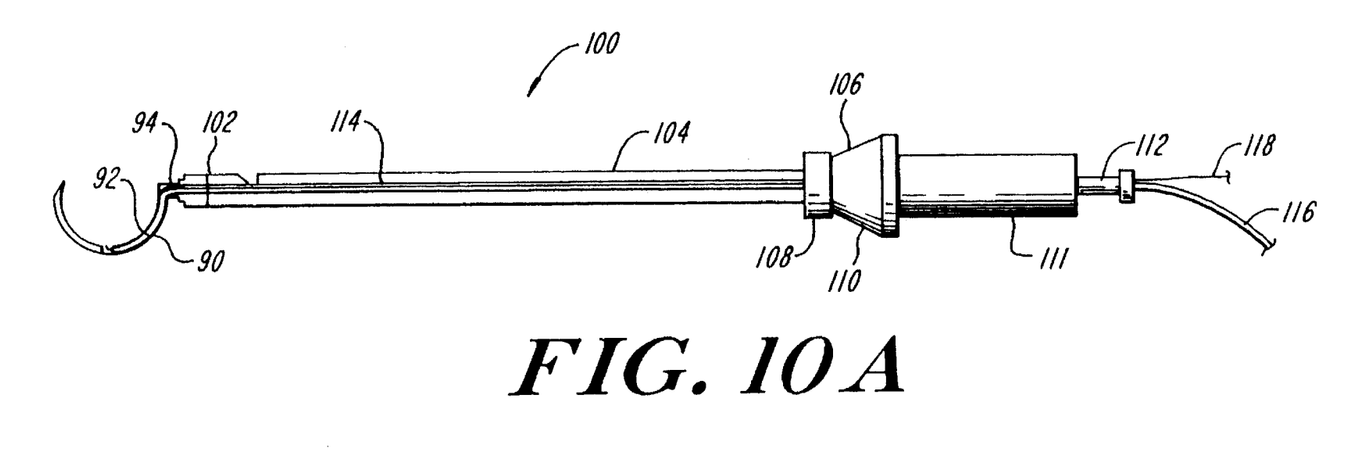
FIG. 10A illustrates a suture needle with an interior passage connected to a needle driver with an interior passage.
Figure 10B:
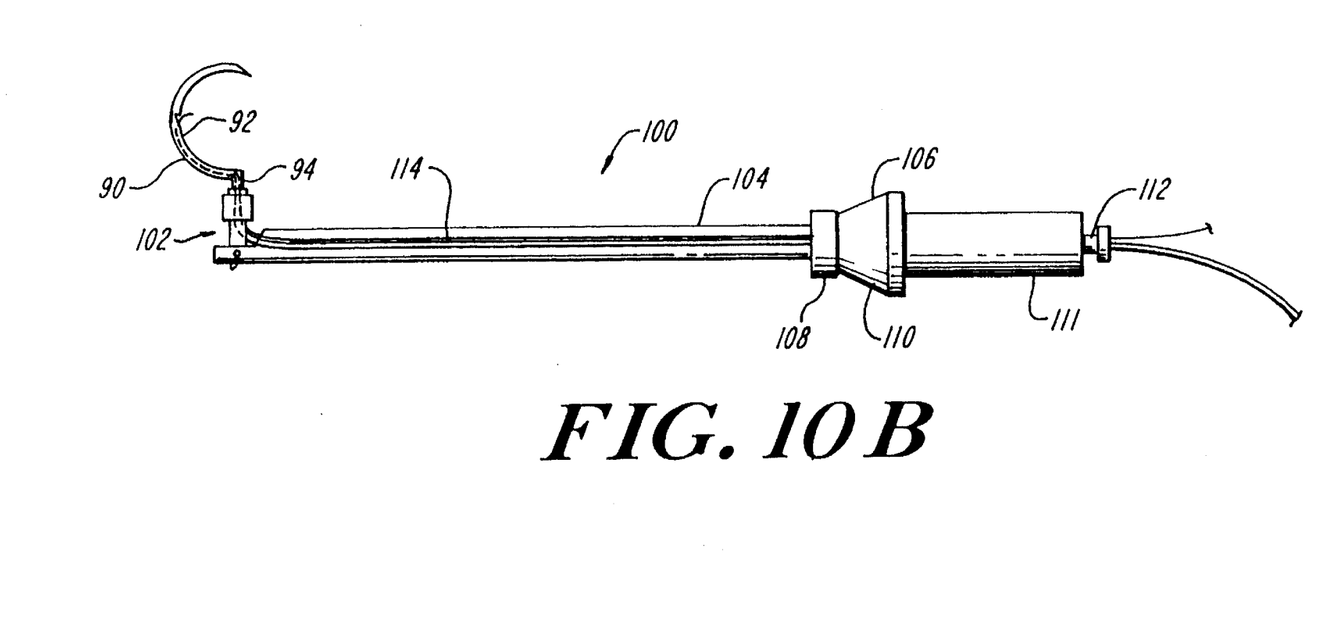
FIG. 10B illustrates the pivoted position of the apparatus.

FIGS. 10A and 10B illustrate another endoscopic needle driver 100 constructed according to the present invention. The needle driver 100 includes a pivoting linkage assembly 102, an extension arm 104, a connecting rod 112 and a handle 111. In the depicted embodiment, the driver 100 further includes the optional rotating cuff 106, which connects between the extension arm 104 and the handle 111.

As illustrated, the coupling arm 94 of the suture needle 90 connects to the linkage assembly 102 located on the distal portion of the extension arm 104. The extension arm 104 connects at its rearward portion to the rotating cuff 106. The rotating cuff 106 has a forward portion 108 and a rearward portion 110 that fits within the forward portion 108. Connecting rod 112 extends through the handle 111 and the extension arm 104.

The endoscopic driver 100 is adapted for use with the needle 90. As illustrated, the needle 90, linkage assembly 102, and connecting rod 112, are constructed with interior passages that couple together within the driver 100 to form the passage 114. The passage 114 extends through the driver 100. In the illustrated embodiment, the passage 114 is adapted to allow suture material 118 and an optional guide wire 116 to enter at the rear of the driver 100. The guide wire 116 and the suture 118 fit snugly within the passage 114 and are frictionally engaged. The interior surface of the passage 114 is sufficiently smooth to allow the wire 116 to move the suture 118 through the connecting rod 112 and through the linkage assembly 102 and to be guided into the needle passage 92. In use, the surgeon can position the suture 118 and the optional guide wire 116 within the driver 100 and the needle 90 before the driver is extended into the laparoscopic port. When the driver 100 is positioned within the laparoscopic port, suture 116 can be driven out the needle port 93 by moving the guide wire 116 further into the driver 100.

FIG. 10A illustrates the needle driver 100 in its initial operating state. In this operating state, the linkage assembly 102 is collinear with the extension arm 104 and the connected needle 90 is disposed in order to fit the driver 100 within a laparoscopic port. In FIG. 10B the driver 100 is shown in the final operating state, with the connecting rod 122 depressed into the handle 111 and the linkage assembly 102 fully actuated so that the needle 90 is disposed perpendicular to the extension arm 104. In the preferred embodiment, the linkage assembly is actuable through a continuous range of positions between the initial state and the final state. FIG. 10A further illustrates the suture and the guide wire in an initial state. As illustrated the suture 118 and the guide wire 116 can be extended within the driver 100 and positioned to be moved through the port 93. FIG. 10B illustrates the driver 100 with the suture 118 extended through the port 93.

It should be apparent to those skilled in the art of surgical device design, that alternative constructions for moving suture through the passage 114 can be implemented without departing from the essence of the invention. For example, the optional guidewire 116 can be replaced with a rod, that loads into the passage 114, and frictionally engages with the suture material to move the suture through the driver 100 and into the needle 90. This and other mechanisms for delivering suture through the opening of the needle 90 are within the contemplation of the present invention.

Figure 11:
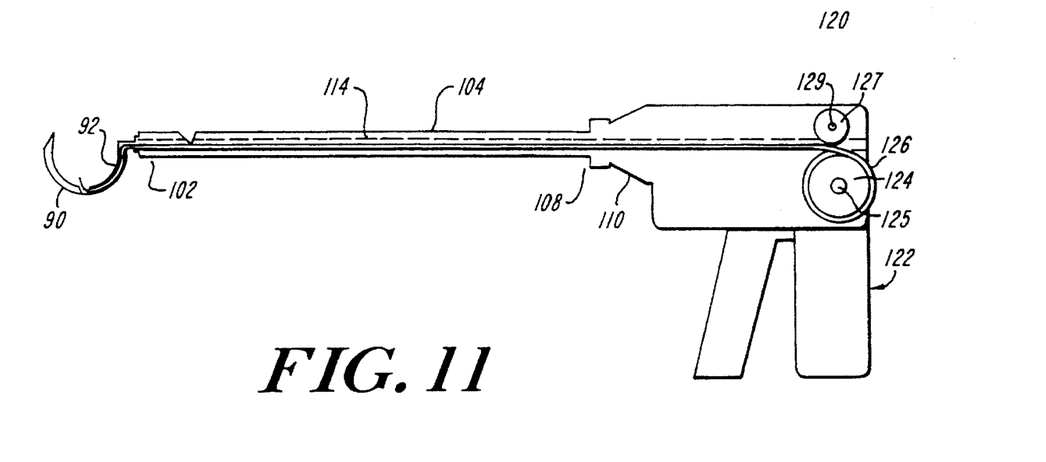
FIG. 11 illustrates a suture needle with an interior passage connected to a needle driver with an interior passage and a pistol grip.

FIG. 11 illustrates a further embodiment of an endoscopic needle driver 120 adapted for use with the needle 90. The illustrated driver 120 has a pistol grip 122 that replaces the handle 111 of the driver 100. The pistol grip 122 works as described above, and actuates the linkage assembly 102 to pivot the needle 90 when the pistol grip 122 is moved from a non-gripping condition to a gripping condition. The driver 120 can further include a rotatable spool of suture 124.

As illustrated in FIG. 11, the rotatable spool 124 can have an axle 125, and a knurled or otherwise textured outer surface 126. A tension wheel 127 mounted on an axle 129 can be located above the spool 124 so that suture delivered from the spool 124 is gripped between the spool 124 and the wheel 127. In one embodiment, the suture initially can be hand fed between the spool 124 and the wheel 127. Once the suture is gripped between the spool 124 and the high friction surface of the wheel 127, the spool 124 and the wheel 127 can be rotated in opposing directions to move the suture forward into the passage 114. In the depicted embodiment, the suture is moved forward into the passage 114 by rotating the spool 124 in a counter-clockwise direction. A gear assembly, not shown, can rotate the wheel 127 in the opposing direction. As depicted, the spool 124 can extend beyond the housing of the pistol grip 122. In operation, the surgeon can rotate the spool 124 in a counter-clockwise direction with his or her thumb so that the suture thread gripped between the wheel 127 and the spool 124 is unwound from the spool 124 and is delivered through the passage 114. The spool and tension wheel assembly illustrated in FIG. 11 is constructed using methods generally known in the art of mechanical linkage design and it should be clear that other mechanisms that move thread-like material can be practiced with the invention. For example, the illustrated apparatus can further include a spool wound with guidewire. The guidewire can be unwound by the spool 124 and the wheel 127 and delivered into the passage 114, along with the suture, to guide the suture down the passage 114.

Figure 12A:
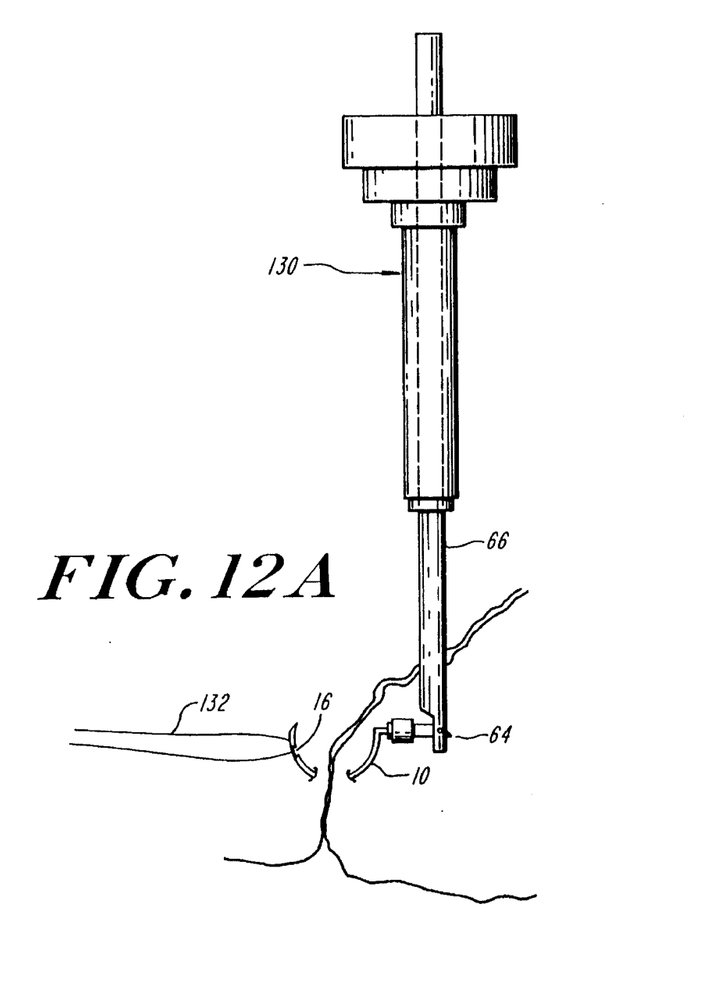
FIGS. 12A and 12B illustrate a method for suturing using a notched suture needle and a needle driver constructed according to the present invention.
Figure 12B:
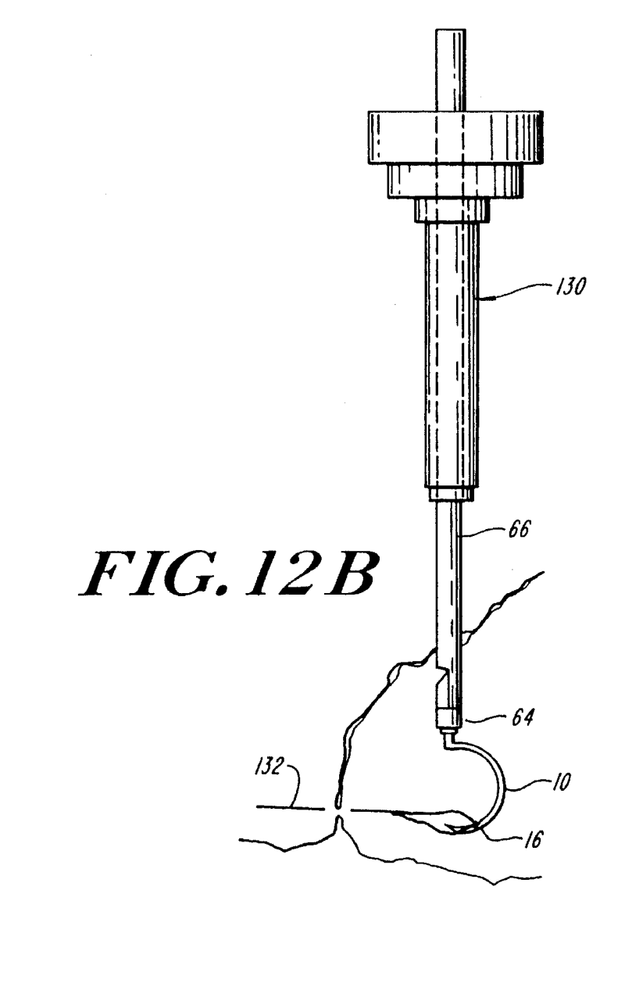

FIGS. 12A and 12B illustrate a further aspect of the present invention, which is a method for suturing tissue using a notched suture needle and a needle driver mechanism. In operation, the surgeon extends the driver 66 into the patient, either through a laparoscopic port or through an anatomical canal such as the urethra. In the typical laparoscopic operation, the surgeon makes three small slits with a surgical trocar. The trocar has a forward cutting portion, a tubular sleeve, a gas port and a retractable handle that is connected to the cutting portion. The cutting portion allows the surgeon to make the small slit and to extend the narrow tubular sleeve into the patient's abdominal cavity. When the sleeve is extended into the patient's abdominal cavity, the surgeon withdraws the handle and the cutting portion, and leaves the hollow sleeve as a laparoscopic port for accessing the abdominal interior. The laparoscopic port connects at the gas port to a source of biologically inert gas. The gas enters the body through the laparoscopic port and inflates the abdominal cavity. When the cavity is inflated, the surgeon extends a video endoscope through one sleeve, and views the surgical site on a video monitor. The methods illustrated in FIGS. 12A and 12B is an endoscopic procedure performed through a laparoscopic port 130. However, the present method also is practicable as a method of suturing through anatomical channels such as the urethra and for suturing delicate tissue such as blood vessels.

As illustrated in FIG. 12A, the surgeon extends the driver 66 through a laparoscopic port 130 and delivers the needle 10 to the anastomotic site. As depicted, the forward portion of the needle 10 is pivoted to penetrate through the tissue segments to be joined. The needle is pivoted, as described above, by a linear actuating force applied to the linkage 64. The linear force can be applied by a pistol grip mechanism, or a simple plunger rod mechanism. The needle 10 is pivoted until the notch 16 penetrates through the tissue and is positioned to receive suture material. A loop of suture 132 is fitted into the notch 16 or a strand of suture is gripped by the U-shaped suture grip, described above, and the suture strand is seated into the notch 16. The needle 10 is retracted through the tissue, and the suture 132 is pulled through to form a stitch. In this way, the suturing procedure is performed with limited lateral movement and without having to pass the suture needle completely through the tissue. The advantages of this technique include allowing the surgeon to suture tissue in restricted anatomical canals, such as the urethra, and to suture without having to release, locate and grasp the suture needle.

Figure 13A:
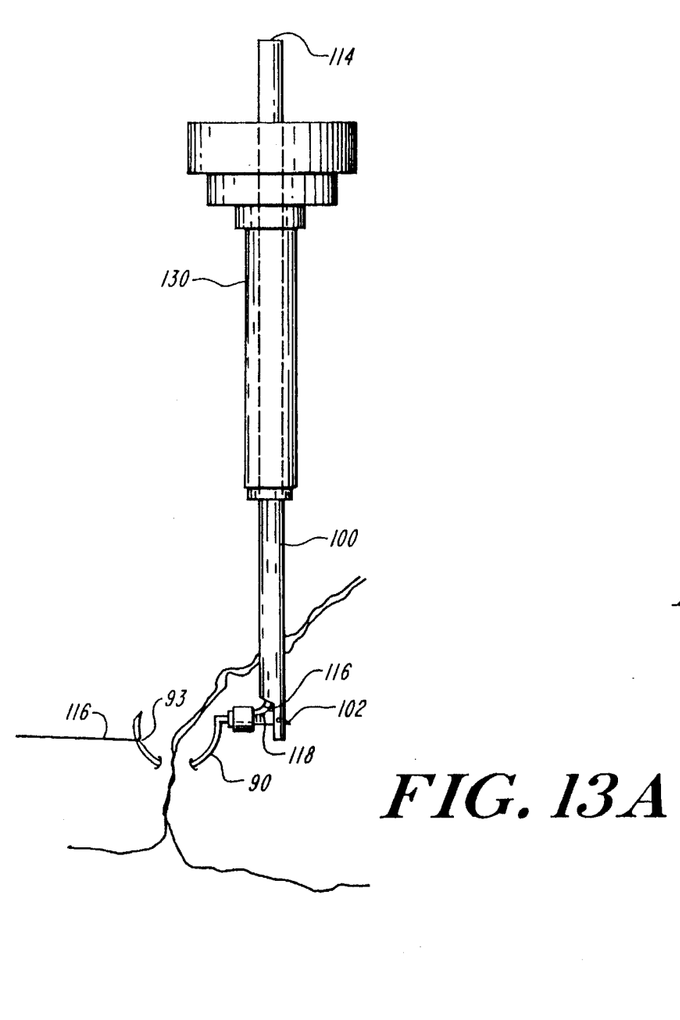
FIGS. 13A and 13B illustrate a method for suturing using a suture needle with an interior passage and a needle driver with an interior passage constructed according to the present invention.
Figure 13B:
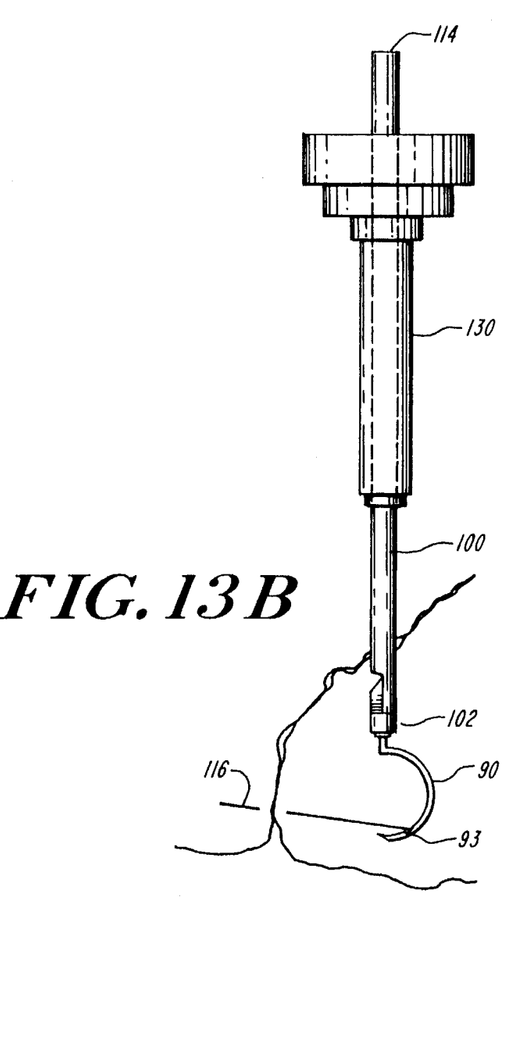

FIGS. 13A and 13B illustrate a further method for suturing according to the present invention. The illustrated method is an endoscopic procedure performed through a laparoscopic port 130. However, the present method also is practicable as a method of suturing through anatomical channels such as the urethra. As illustrated in FIG. 13A, the surgeon extends the driver 100 through a laparoscopic port 130 and delivers the needle 90 to the anastomotic site. As depicted, the forward portion of the needle 90 is pivoted to penetrate through the tissue to be joined. The forward portion of the needle 90 penetrates through the tissue until the port 93 extends through. The surgeon directs the guide wire 118 through the interior passage 114 to move the suture 116 through the passage 114 until it extends through the port 93. The surgeon grips the suture 116 and retracts the needle 90 through the tissue to form a stitch within the tissue segments.

The present invention allows for the construction of suture needles and needle driver mechanisms specially adapted for use in endocsopic surgery or catheterization procedures. The needle is constructed to include means to deliver suture through tissue segments as the needle is retracted from the segments. In operation, only the distal end of the needle is passed through the tissue segments to be joined. In the preferred embodiment, the distal end of the needle has the means to deliver suture through the tissue as the needle retracts. In one embodiment, suture is seated within a notch on the needle distal end and the needle is retracted through the tissue to form a stitch. In a further embodiment of the invention the notched suture needle is used in cooperation with a needle driver mechanism. The needle driver mechanism is a long, slender extension arm adapted for fitting within a laparoscopic port. The extension arm can house a linkage assembly at the distal portion of the extension arm and the linkage assembly connects to the notched suture needle. The linkage assembly also connects to a plunger extending rearward from the linkage assembly and projecting outward from the extension arm. By driving the connecting rod forward, the linkage assembly is operated and pivots the suture needle. In this way, a linear motion at the rearward portion of the needle pivots the suture needle into the tissue to be joined. This construction allows for the surgeon to perform the suture operation with limited lateral movement. In another embodiment, the needle has an interior passage and a port that can be used to feed suture through the needle. In use, the needle penetrates the tissue to be joined, and the suture is fed through the needle to the opposite side of the anastomotic site. When the needle is retracted, the suture is drawn through the tissue and a stitch is formed.

In a further aspect of the invention, a suture grip adapted to form a loop of suture, is used in cooperation with the notched suture needle in order to more easily fit a loop of suture within the needle notch. This suture grip is constructed as an endoscopic instrument having a U-shaped head adapted for grasping suture in such a manner that a strand of suture is extended between the two arms of the U-shaped head. The surgeon fits the U-shaped head over the suture needle and seats the extended strand of suture into the notch.

What is claimed:

1. Suturing apparatus for endoscopic suturing, comprising a curved needle dimensionally adapted for fitting through an endoscopic port and having a pointed distal end portion, a proximal end portion adapted to form a mounting element, and engagement means for receiving suture and for holding the suture at a position between said distal and proximal ends; and an arm having a distal end which couples to said needle mounting element to carry said curved needle at said distal arm end with said pointed portion of said needle extending outward from said arm, a linkage located at said distal portion of said arm and including means for pivoting said needle relative to an axis extending transversely to said arm, whereby tissue segments can be joined by piercing the tissue segments with said needle, engaging the suture with the needle and pivoting said needle to draw the suture through the tissue segments.

2. Suturing apparatus according to claim 1, wherein said engagement means for receiving suture is a notch.

3. Suturing apparatus according to claim 2 further comprising a latch means connected to said needle for providing closure of a suture within said notch.

4. Suturing apparatus according to claim 3 wherein said latch is biased in a closed position.

5. Suturing apparatus according to claim 1, wherein said engagement means for receiving suture is a V-shaped notch adapted for pulling suture through tissue.

6. Suturing apparatus according to claim 1 wherein said engagement means for receiving suture is located adjacent to said distal end of said curved needle.

7. Suturing apparatus according to claim 1 wherein said engagement means for receiving suture is located on an interior surface of said curved needle.

8. Suturing apparatus according to claim 1 wherein said engagement means for receiving suture is located on an interior surface and said needle possesses an exterior surface which is substantially smooth.

9. Suturing apparatus according to claim 1 wherein said engagement means for receiving suture is located on an exterior surface of said curved needle.

10. Suturing apparatus according to claim 1 wherein said curved needle is a substantially flat blade and at least one surface further comprises a cutting edge.

11. Suturing apparatus according to claim 1 further comprising an interior passage extending between said engagement means and an opening on a surface of said needle.

12. Suturing apparatus according to claim 11 wherein said interior passage extends between said engagement means and an opening at the proximal end portion of said needle.

13. Suturing apparatus according to claim 11 further comprising guiding means, coupled to said needle, for moving suture through said interior passage and out said engagement means.

14. Suturing apparatus according to claim 1 wherein said arm comprises mounting means coupled to said distal end of said arm for removably and replaceably connecting a disposable needle at said distal arm end.

15. Suturing apparatus according to claim 1 wherein said arm comprises rotational means for rotating said needle relative to an axis extending parallel to said arm to vary the angular orientation of said needle.

16. Suturing apparatus according to claim 1 further comprising a grip assembly connecting to the rearward portion of said arm, said grip assembly further comprising a triggering means coupled to said linkage to affect pivoting action of said needle.

17. Suturing apparatus according to claim 1 further comprising an interior passage extending along a longitudinal axis of said arm and connecting to an opening at said distal arm end.

18. Suturing apparatus according to claim 17 further comprising guiding means, coupled to said arm, for moving suture through said arm interior passage.

19. Suturing apparatus according to claim 17 further comprising storage means, connected to said guiding means, and adapted for storing suture and for providing suture to said guiding means.

20. A method for suturing comprising the steps of providing a curved needle having a pointed distal end, an interior passage for receiving suture, an opening in a surface of said needle, and a mounting element that mounts said needle to an arm having an interior passage for delivering suture, and having a linkage assembly that includes pivoting means for pivoting said needle relative to an axis transverse to said arm pivoting said needle about the transverse axis to pass said pointed end and said opening through tissue, guiding suture through said interior passage within said arm, into said interior passage of said needle and through said opening, gripping said suture extending through said opening, and pivoting said needle to retract said needle through the tissue.

21. A kit for suturing tissue, comprising a curved needle having a pointed distal end portion, a proximal end portion and engagement means, disposed between said distal and proximal ends for receiving suture;

an arm having coupling means for coupling said curved needle to a distal end of said arm; and having a linkage assembly that includes pivoting means for pivoting of said needle relative to an axis transverse to said arm; and a suture grip having means for grasping suture at two separate locations.

22. A method for suturing comprising the steps of providing a curved needle having a pointed distal end, a notch for receiving suture and a mounting element that mounts said needle to an arm having a linkage assembly that includes pivoting means for pivoting said needle, pivoting said needle about an axis transverse to said arm to pass said pointed end and said notch through tissue, securing the suture within said notch by gripping suture material at a first location and at a second location and fitting the suture material extending between said first and said second location within said notch, and retracting said needle through the tissue.

23. Suturing apparatus for endoscopic surgery, comprising a curved needle being dimensionally adapted for fitting through an endoscopic port and having a pointed distal end portion, a proximal end portion, and a notch disposed between said distal and proximal end portions and adapted for receiving suture, an arm having a distal end and being dimensionally adapted for extending said distal end through an endoscopic port for positioning said distal end proximate to an anastomotic site, and a linkage assembly that includes pivoting means coupled to said distal end of said arm and to said needle to carry said needle at said distal end with said pointed portion extending outward from said arm, said pivoting means being adapted for pivoting said needle about an axis transverse to said arm.

24. Suturing apparatus for endoscopic surgery, comprising a curved needle being dimensionally adapted for fitting through an endoscopic port and having a pointed distal end portion and a proximal end portion, an interior passage extending partly between said distal and proximal end portions and connecting to an opening at said proximal end, and a notch disposed between said distal and proximal end portions and arranged to form an opening into said interior passage, and an arm having an interior passage extending substantially parallel to said arm and connecting to an opening at a distal end of said arm, wherein said distal arm end is adapted to couple to said proximal end portion of said needle to form, in cooperation with said needle, an interior passage extending between said arm and said needle, guiding means, coupled to said arm, for providing suture into said arm interior passage and for moving suture through said arm interior passage, into said needle interior passage and out said notch, and a linkage assembly disposed at said distal end of said arm and having pivoting means for pivoting said needle about an axis transverse to said arm, whereby tissue segments can be joined by piercing the tissue segments with said needle, guiding suture through said passage and out said notch and pivoting said needle to draw the suture through the tissue segments.

* * * * *